(12) United States Patent  (10) Patent No.: US 8,961,434 B2
Miyata et al.  (45) Date of Patent: Feb. 24, 2015

(54) MEDICAL GUIDEWIRE

(75) Inventors: Naohiko Miyata, Nagoya (JP); Satoshi Nagano, Nagoya (JP); Makoto Nishigishi, Nagoya (JP)

(73) Assignee: Asahi Intecc Co., Ltd., Nagoya (JP)

( * ) Notice: Subject to any disclaimer, the term of this patent is extended or adjusted under 35 U.S.C. 154(b) by 0 days.

(21) Appl. No.: 13/327,470

(22) Filed: Dec. 15, 2011

(65) Prior Publication Data

US 2012/0089127 A1 Apr. 12, 2012

Related U.S. Application Data

(63) Continuation of application No. 12/813,053, filed on Jun. 10, 2010.

(30) Foreign Application Priority Data

Jun. 16, 2009 (JP) ................................ 2009-143570

(51) Int. Cl.
*A61B 5/00* (2006.01)
*A61M 25/00* (2006.01)
*A61M 25/09* (2006.01)

(52) U.S. Cl.
CPC ..... *A61M 25/09* (2013.01); *A61M 2025/09083* (2013.01); *A61M 2025/09175* (2013.01)
USPC ...................................................... 600/585

(58) Field of Classification Search
USPC ...................................................... 600/585
See application file for complete search history.

(56) References Cited

U.S. PATENT DOCUMENTS

| 5,345,945 | A | 9/1994 | Hodgson et al. |
| 5,377,690 | A | 1/1995 | Berthiaume |
| 5,551,444 | A | 9/1996 | Finlayson |
| 5,833,631 | A | 11/1998 | Nguyen |
| 6,544,197 | B2 | 4/2003 | DeMello |
| 7,077,811 | B2 * | 7/2006 | Vrba et al. ............ 600/585 |
| 7,117,703 | B2 | 10/2006 | Kato et al. |
| 7,252,643 | B2 | 8/2007 | Fujimoto et al. |
| 7,322,944 | B2 | 1/2008 | Osawa et al. |
| 7,753,859 | B2 | 7/2010 | Kinoshita et al. |

(Continued)

FOREIGN PATENT DOCUMENTS

| CN | 1537645 A | 10/2004 |
| DE | 20 2005 007 570 U1 | 9/2005 |

(Continued)

OTHER PUBLICATIONS

JP Office Action with English summary and English translation for JP Application No. 2009-143732 mailed on Apr. 22, 2011.

(Continued)

*Primary Examiner* — Devin Henson
(74) *Attorney, Agent, or Firm* — Oliff PLC

(57) ABSTRACT

Provided is a guidewire including a core shaft, an outer flexible tube, a stranded wire that extends parallel to the core shaft, and a hollow stranded-wire coil disposed in the outer flexible tube. The hollow stranded-wire coil is formed of multiple strands and surrounds the distal end portion of the core shaft and the stranded wire. Distal ends of the hollow stranded-wire coil, the core shaft, and the stranded wire are joined to a distal end of the outer flexible tube.

8 Claims, 4 Drawing Sheets

(56) References Cited

U.S. PATENT DOCUMENTS

| | | | |
|---|---|---|---|
| 7,785,273 B2 * | 8/2010 | Eskuri | 600/585 |
| 7,833,175 B2 | 11/2010 | Parins | |
| 7,878,984 B2 * | 2/2011 | Jacobsen et al. | 600/585 |
| 7,883,474 B1 | 2/2011 | Mirigian et al. | |
| 7,914,467 B2 | 3/2011 | Layman et al. | |
| 7,951,091 B2 | 5/2011 | Segner et al. | |
| 8,267,872 B2 | 9/2012 | Ressemann et al. | |
| 2004/0116833 A1 | 6/2004 | Kato et al. | |
| 2004/0122340 A1 | 6/2004 | Vrba et al. | |
| 2004/0167442 A1 | 8/2004 | Shireman et al. | |
| 2004/0181174 A2 | 9/2004 | Davis et al. | |
| 2004/0210163 A1 | 10/2004 | Osawa et al. | |
| 2005/0065456 A1 | 3/2005 | Eskuri | |
| 2006/0014418 A1 | 1/2006 | Kato et al. | |
| 2007/0083132 A1 * | 4/2007 | Sharrow | 600/585 |
| 2008/0045908 A1 | 2/2008 | Gould et al. | |
| 2008/0214959 A1 | 9/2008 | Miyata et al. | |
| 2008/0262474 A1 * | 10/2008 | Northrop | 604/529 |
| 2008/0281230 A1 | 11/2008 | Kinoshita et al. | |
| 2009/0036832 A1 | 2/2009 | Skujins et al. | |
| 2009/0076416 A1 | 3/2009 | Treacy et al. | |
| 2009/0112127 A1 | 4/2009 | Keating et al. | |

FOREIGN PATENT DOCUMENTS

| | | |
|---|---|---|
| EP | 0 611 073 A1 | 8/1994 |
| EP | 1 243 283 A2 | 9/2002 |
| EP | 1 468 707 A1 | 10/2004 |
| EP | 1 498 152 A1 | 1/2005 |
| JP | A-06-292729 | 10/1994 |
| JP | 07-080076 A | 3/1995 |
| JP | 08-173547 A | 7/1996 |
| JP | A-08-173547 | 7/1996 |
| JP | 09-182800 A | 7/1997 |
| JP | A-9-182800 | 7/1997 |
| JP | A-10-066728 | 3/1998 |
| JP | A-2002-539901 | 11/2002 |
| JP | 2004-190167 A | 7/2004 |
| JP | A-2004-190167 | 7/2004 |
| JP | 2004-313570 A | 11/2004 |
| JP | 2006-511304 A | 4/2006 |
| JP | A-2006-519072 | 8/2006 |
| JP | 2008-161491 A | 7/2008 |
| JP | A-2008-307367 | 12/2008 |
| WO | WO 98/18516 | 5/1998 |
| WO | WO 00/57944 | 10/2000 |
| WO | 2006/002199 A2 | 1/2006 |
| WO | 2004/060462 A2 | 7/2007 |

OTHER PUBLICATIONS

Extended EP Search Report dated Oct. 18, 2010 for corresponding EP Application No. 10165916.7.
Extended EP Search Report dated Mar. 14, 2012 for corresponding EP Application No. 11195917.7.
Feb. 26, 2013 Office Action issued in Japanese Patent Application No. 2011-267323 (w/translation).
Mar. 26, 2013 Notification of Reason for Refusal issued in Japanese Patent Application No. 2011-283628 (with translation).
Japanese Office Action issued in Japanese Patent Application No. 2011-283628 dated Oct. 7, 2013 (w/ translation).
Nov. 7, 2012 Office Action issued in U.S. Appl. No. 12/813,053.
Apr. 9, 2013 Office Action issued in U.S. Appl. No. 12/813,053.
Jul. 11, 2014 Office Action issued in U.S. Appl. No. 12/813,053.
Jul. 14, 2014 Office Action issued in U.S. Appl. No. 13/424,994.
Aug. 26, 2014 Interview Summary issued in U.S. Appl. No. 12/813,053.
Oct. 13, 2010 Extended European Search Report issued in Application No. 10165921.7.
Sep. 25, 2012 Extended European Search Report issued in Application No. 12176410.4.
Aug. 27, 2012 Office Action issued in Chinese Application No. 201010206573.1 (with English Translation).
Oct. 16, 2012 Office Action issued in Chinese Application No. 201110424164.3 (with English Translation).
Feb. 17, 2013 Office Action issued in Chinese Application No. 201010206573.1 (with English Translation).
May 15, 2013 Office Action issued in Chinese Application No. 201210065819.7 (with English Translation).
May 16, 2013 Office Action issued in Chinese Application No. 201110424164.3 (with English Translation).
Aug. 1, 2013 Office Action issued in Chinese Application No. 201210065819.7 (with English Translation).
Oct. 23, 2013 Office Action issued in Chinese Application No. 201110424164.3 (with English Translation).
May 13, 2014 Office Action issued in Chinese Application No. 201010206573.1 (with English Translation).
Apr. 22, 2011 Office Action issued in Japanese Application No. 2009-143570 (with English Translation).
Nov. 17, 2011 Office Action issued in Japanese Application No. 2009-143570 (with English Translation).
Nov. 5, 2014 Office Action issued in Japanese Patent Application No. 2013-252827 w/translation.
Sep. 29, 2014 Office Action issued in Chinese Patent Application No. 2010-10206573.1 w/translation.
Nov. 24, 2014 Office Action issued in U.S. Appl. No. 13/424,994.

* cited by examiner

MEDICAL GUIDEWIRE

BACKGROUND OF THE INVENTION

1. Field of the Invention

The present invention relates to a medical guidewire used for medical purposes such as inserting a catheter into a blood vessel, a ureter, or an organ or inserting an indwelling device into part of a blood vessel suffering from an aneurysm.

2. Description of the Related Art

In general, it is required that a medical guidewire have a flexible distal end portion. In order to fulfill such a requirement, a guidewire 100 of the related art includes a core shaft 101 and a coil spring 102 that surrounds the core shaft 101, and the diameter of a distal end portion 103 of the core shaft 101 is made small so as to improve flexibility (see FIG. 4).

When using the guidewire 100 to guide a device, such as a catheter or an indwelling device, to a target region in a human body, the distal end portion of the guidewire 100 may be unintentionally bent into a U-shape. For some operations, the guidewire 100 is bent into a U-shape before insertion in order to prevent misinsertion of the guidewire 100 into a nontarget blood vessel or in order that the guidewire 100 is securely held by a blood vessel wall by using the resilience of the guidewire 100.

The guidewire 100 of the related art has a low rigidity because the diameter of the distal end portion 103 of the core shaft 101 is small, so that the guidewire 100 is easily bent due to stress concentration. Once the core shaft 101 is bent into a U-shape, plastic deformation occurs, so that the core shaft 101 has a residual angle even after the U-shaped bending is released. Due to the presence of the residual angle, the operability of the guidewire 100 is reduced, and the guidewire 100 may have to be replaced during the operation.

It is required that the guidewire 100 have a flexible and resilient distal end portion, and it is also required that the guidewire 100 has a good torque transmission with which an operation performed at the proximal end portion is smoothly transmitted to the distal end portion.

A modification of the guidewire 100 uses a stranded wire as the distal end portion 103 of the core shaft 101 (see Japanese Unexamined Patent Application Publication No. 2008-161491). The guidewire 100 has a certain degree of resilience after having been bent. However, when the guidewire 100 is bent into a U-shape having a large curvature, the guidewire 100 may not recover its original shape even after the U-shaped bending is released. Therefore, the drawback due to the presence of a residual angle remains.

Another modification of the guidewire 100 includes a radiopaque inner coil disposed between the coil spring 102 and the core shaft 101 (see Japanese Unexamined Patent Application Publication No. 08-173547 and Japanese Unexamined Patent Application Publication (Translation of PCT Application) No. 2006-511304). With the guidewire 100, the rigidity of a part of the distal end portion 103 having the inner coil is increased. However, this modification also has the drawback due to the presence of a residual angle after having been bent into a U-shape.

SUMMARY OF THE INVENTION

The object of the present invention, which has been achieved in order to overcome the drawback described above, is to provide flexibility and resilience to a distal end portion of a medical guidewire and to improve the torque transmission of the medical guidewire.

According to an aspect of the present invention, there is provided a medical guidewire (hereinafter referred to as a "guidewire") including a core shaft including a distal end portion having a small diameter; an outer flexible tube that surrounds an outer surface of the core shaft; a stranded wire disposed parallel to the distal end portion of the core shaft; and a hollow stranded-wire coil disposed in the outer flexible tube, the hollow stranded-wire coil being formed of multiple strands and surrounding the distal end portion of the core shaft and the stranded wire. Distal ends of the hollow stranded-wire coil, the core shaft, and the stranded wire are joined to a distal end of the outer flexible tube.

The strands of the stranded wire can move slightly relative to each other. Therefore, the stranded wire has a high degree of freedom, a high flexibility, a high resistance to plastic deformation, and a high resilience. Therefore, by disposing the stranded wire parallel to the distal end portion of the core shaft, the flexibility of the guidewire is maintained and the resilience of the guidewire after being bent into a U-shape is improved.

The hollow stranded-wire coil, which is formed of multiple strands, is disposed in the outer flexible tube and surrounds the distal end portion of the core shaft and the stranded wire. The distal ends of the hollow stranded-wire coil, the core shaft, and the stranded wire are joined to the distal end of the outer flexible tube. The hollow stranded-wire coil, which is formed of multiple strands, has a better torque transmission than a single-wire coil. By disposing the distal end of the hollow stranded-wire coil at the distal end of the guidewire in the joined state, the guidewire can smoothly transmit an operation performed at the proximal end portion to the distal end portion. Therefore, a user can operate the guidewire at will, so that the treatment time can be reduced. Moreover, the hollow stranded-wire coil has a better resilience than a single coil. Therefore, by surrounding outer surfaces of the core shaft and the stranded wire with the hollow stranded-wire coil, the resilience of the distal end portion of the guidewire can be improved.

DESCRIPTION OF THE PREFERRED EMBODIMENTS

A medical guidewire according to a first embodiment includes a core shaft including a distal end portion having a small diameter; an outer flexible tube that surrounds an outer surface of the core shaft; a stranded wire disposed parallel to the distal end portion of the core shaft; and a hollow stranded-wire coil disposed in the outer flexible tube, the hollow stranded-wire coil being formed of multiple strands and surrounding the distal end portion of the core shaft and the stranded wire. Distal ends of the hollow stranded-wire coil, the core shaft, and the stranded wire are joined to a distal end of the outer flexible tube.

The outer diameter of the core shaft decreases stepwise toward the distal end. The hollow stranded-wire coil is made by stranding multiple metal strands. The hollow stranded-wire coil has a tapered shape in which the outside diameter gradually decreases toward the distal end. The inside diameter of the hollow stranded-wire coil is uniform from the distal end to the proximal end. The metal strands of the hollow stranded-wire coil are made of a stainless steel alloy.

First Embodiment

Structure of First Embodiment

Figure 1:
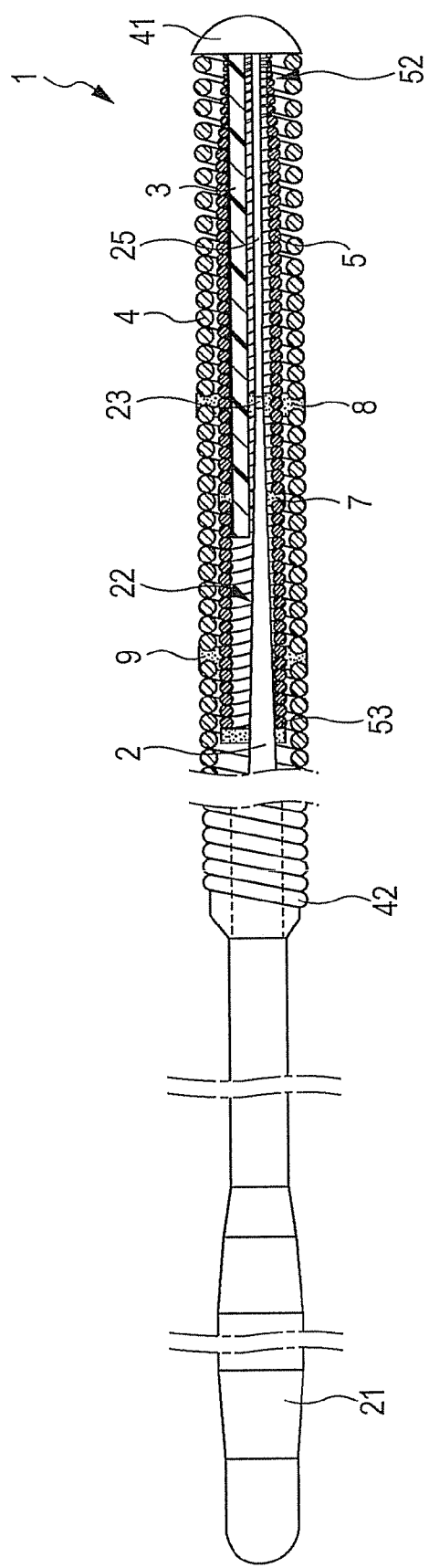
FIG. 1 is a partially sectional side view of a guidewire according to a first embodiment.
Figure 2:
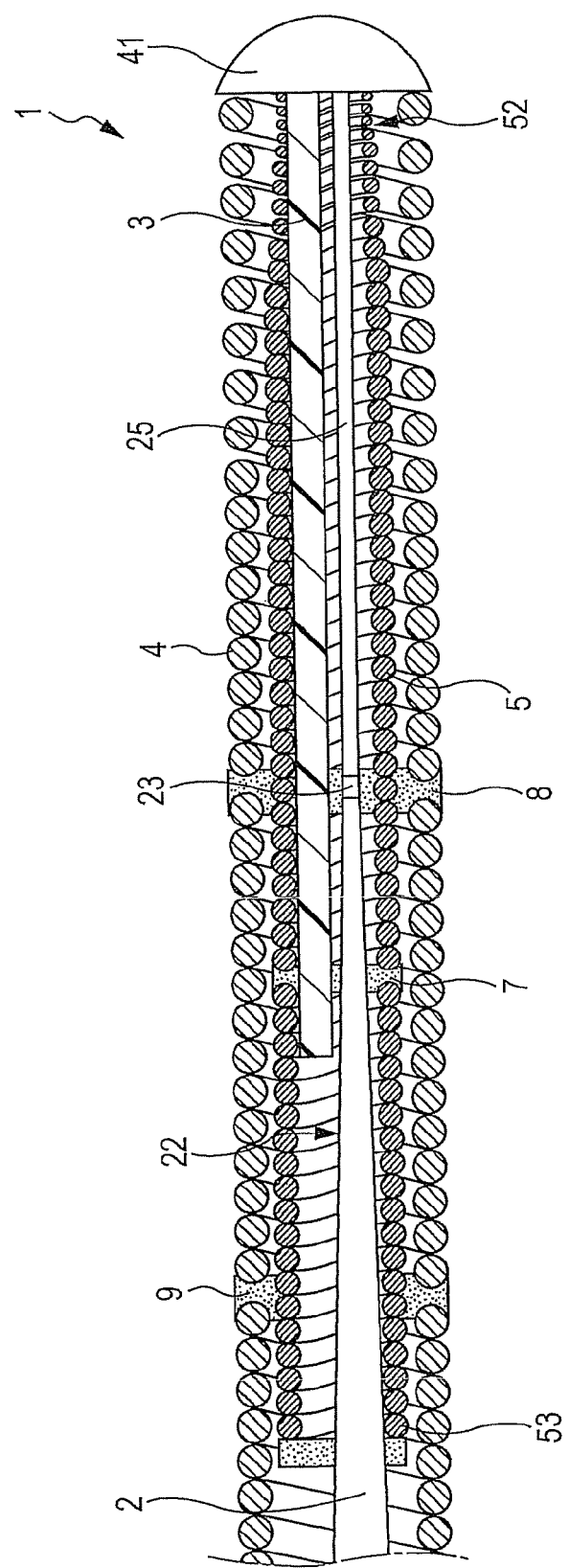
FIG. 2 is a sectional side view of a distal end portion of the guidewire according to the first embodiment.

Referring to FIGS. 1 and 2, the structure of a guidewire 1 according to the first embodiment will be described. In FIGS. 1 and 2, the right side is the distal end side, and the left side is the proximal end side. The guidewire 1 includes a core shaft 2, a stranded wire 3 disposed parallel to the core shaft 2, an outer flexible tube 4 through which the core shaft 2 and the stranded wire 3 are inserted, and a hollow stranded-wire coil 5 disposed in the outer flexible tube 4. The core shaft 2 and the stranded wire 3 are inserted through the hollow stranded-wire coil 5. The core shaft 2, the stranded wire 3, and the hollow stranded-wire coil 5 are inserted through the outer flexible tube 4.

The core shaft 2 is made of a stainless steel alloy. The core shaft 2 has a grip 21, which has a large diameter, positioned adjacent to the proximal end thereof and a distal end portion 22, which has a small diameter, positioned adjacent to the distal end thereof. The diameter of the distal end portion 22 of the core shaft 2 decreases stepwise. The distal end portion 22 of the core shaft includes a step portion 23 and a small-diameter portion 25 that extends from the step portion 23 to the distal end of the core shaft 2. In the first embodiment, the outside diameter of the small-diameter portion 25 is 0.03 mm.

The stranded wire 3 is made by stranding metal strands made of, for example, a stainless steel alloy. In the first embodiment, for example, the stranded wire 3 is made by stranding seven stainless steel strands each having an outside diameter of 0.014 mm. The stranded wire 3 is disposed parallel to the distal end portion 22 of the core shaft 2. A distal end of the stranded wire 3 and the distal end of the core shaft 2 are soldered to a brazed end portion 41 disposed at the distal end of the outer flexible tube 4. A proximal end of the stranded wire 3 is positioned between the proximal end of the small-diameter portion 25 and the proximal end of the core shaft 2. The proximal end of the stranded wire 3 and the core shaft 2 are soldered to the hollow stranded-wire coil 5 at a position between the step portion 23 and the proximal end of the core shaft 2 (a soldered portion 7).

The outer flexible tube 4 is a single-wire coil made of a stainless steel strand. In the first embodiment, for example, the stainless steel strand has an outside diameter of 0.05 mm and the outer flexible tube 4 has an outside diameter of 0.355 mm. In order to provide flexibility to the distal end portion of the outer flexible tube 4, the pitch of a distal end portion of the outer flexible tube 4 is enlarged. As long as the outer flexible tube 4 has flexibility, the outer flexible tube 4 need not be a single-wire coil and may instead be a hollow stranded-wire coil, a resin tube, or the like.

The outer flexible tube 4 surrounds only a distal end portion of the core shaft 2. A proximal end 42 of the outer flexible tube 4 is fixed to an outer surface of a large-diameter portion of the core shaft 2 near to the proximal end of the core shaft 2. An outer surface of the outer flexible tube 4 is coated with a hydrophilic resin.

The hollow stranded-wire coil 5 is made by stranding multiple stainless steel strands around a core by using a wire stranding machine and then removing the core, or by stranding multiple strands into a hollow shape. In the first embodiment, for example, the hollow stranded-wire coil 5, which has an outside diameter of 0.188 mm, is formed by stranding six stainless steel strands each having an outside diameter of 0.04 mm, so that the flexibility and the torque transmission are well balanced. A distal end portion 52 of the hollow stranded-wire coil 5 is electro-polished so that the outside diameter decreases toward the distal end. The inside diameter of the hollow stranded-wire coil 5 is uniform from the proximal end to the distal end.

The hollow stranded-wire coil 5 has an outside diameter that is smaller than the inside diameter of the outer flexible tube 4. The hollow stranded-wire coil 5 has a length in the axial direction that is smaller than that of the outer flexible tube 4. A proximal end 53 of the hollow stranded-wire coil 5 is positioned between the proximal end 42 of the outer flexible tube 4 and the distal end of the outer flexible tube 4 in the axial direction. The hollow stranded-wire coil 5 and the outer flexible tube 4 are fixed to each other at least one position so that relative positions thereof are fixed. In the first embodiment, the hollow stranded-wire coil 5, the outer flexible tube 4, the stranded wire 3, and the core shaft 2 are fixed to each other by soldering at a position corresponding to the step portion 23 (a soldered portion 8). Moreover, the hollow stranded-wire coil 5 and the outer flexible tube 4 are fixed to each other at a position between the proximal end of the stranded wire 3 and the proximal end of the outer flexible tube 4 in the axial direction (a soldered portion 9).

The proximal end 53 of the hollow stranded-wire coil 5 is positioned between the step portion 23 and the proximal end of the core shaft 2 and between the proximal end of the stranded wire 3 and the proximal end of the core shaft 2. Moreover, as described above, the distal ends of the hollow stranded-wire coil 5, the core shaft 2, and the stranded wire 3 are fixed to the brazed end portion 41 at the distal end of the outer flexible tube 4. The proximal end 53 of the hollow stranded-wire coil 5 is fixed to the outer surface of the core shaft 2.

Operational Effect of First Embodiment

In the guidewire 1 of the first embodiment, the stranded wire 3 is disposed parallel to the distal end portion 22 of the core shaft 2. The diameter of the distal end portion 22 of the core shaft 2 decreases stepwise toward the distal end. The strands of the stranded wire 3 can move slightly relative to each other. Therefore, the stranded wire 3 has a high degree of freedom, a high flexibility, a high resistance to plastic deformation, and a high resilience. Therefore, by disposing the stranded wire 3, which has resistance to plastic deformation, parallel to the distal end portion 22 of the core shaft 2, which has a small diameter and thus has flexibility, the resilience of the guidewire 1 after being bent into a U-shape is improved while maintaining the flexibility of the guidewire 1.

The guidewire 1 includes the hollow stranded-wire coil 5, which is disposed in the outer flexible tube 4 and surrounds the distal end portion 22 of the core shaft 2 and the stranded wire 3. The distal ends of the hollow stranded-wire coil 5, the core shaft 2, and the stranded wire 3 are joined to the distal end of the outer flexible tube 4. The hollow stranded-wire coil 5, which is formed of multiple strands, has a better torque transmission than a single-wire coil. By joining the distal end of the hollow stranded-wire coil 5 to the distal end of the outer flexible tube 4 and disposing the distal end of the hollow stranded-wire coil 5 at the distal end of the guidewire 1, the guidewire 1 can smoothly transmit an operation performed at the proximal end portion to the distal end portion. Therefore, a user can operate the guidewire 1 at will, so that the treatment time can be reduced. Moreover, the hollow stranded-wire coil 5 has a better resilience than a single coil. Therefore, by surrounding outer surfaces of the core shaft 2 and the stranded wire 3 with the hollow stranded-wire coil 5, the resilience of the distal end portion of the guidewire 1 can be improved.

The distal end portion 52 of the hollow stranded-wire coil 5 has a tapered shape in which the diameter gradually decreases toward the distal end. Therefore, the guidewire 1 has a structure having a gradation in rigidity in which the rigidity gradually increases toward the proximal end, and occurrence of stress concentration due to a sharp difference in rigidity is suppressed, so that the torque transmission is improved. The distal end portion of the hollow stranded-wire coil 5 has a small diameter, so that the flexibility of the guidewire 1 is improved and the guidewire 1 can be more easily inserted into a peripheral lumen.

The inside diameter of the hollow stranded-wire coil 5 is uniform from the distal end to the proximal end. Therefore, the core shaft 2 and the stranded wire 3 can be easily inserted into the hollow stranded-wire coil 5, so that the guidewire 1 can be easily assembled.

The metal strands of the hollow stranded-wire coil 5 are made of a stainless steel alloy. Therefore, the rigidity of the hollow stranded-wire coil 5 is increased, so that the torque transmission and the operability of the guidewire 1 are improved.

Modification

In the first embodiment, the diameter of the distal end portion 22 of the core shaft 2 decreases stepwise toward the distal end. Alternatively, the distal end portion 22 may be tapered toward the distal end.

In the first embodiment, the core shaft 2 is made of a stainless steel alloy. Alternatively, a part of the core shaft 2 near to the distal end (at least the small-diameter portion 25) may be made of a pseudoelastic alloy having a high resilience (for example, Ni—Ti alloy), and a part of the core shaft 2 near to the proximal end may be made of a stainless steel alloy. With this structure, the resilience of the distal end portion of the guidewire 1 can be improved, and the torque transmission and the operability of the guidewire 1 can be improved.

Figure 3:
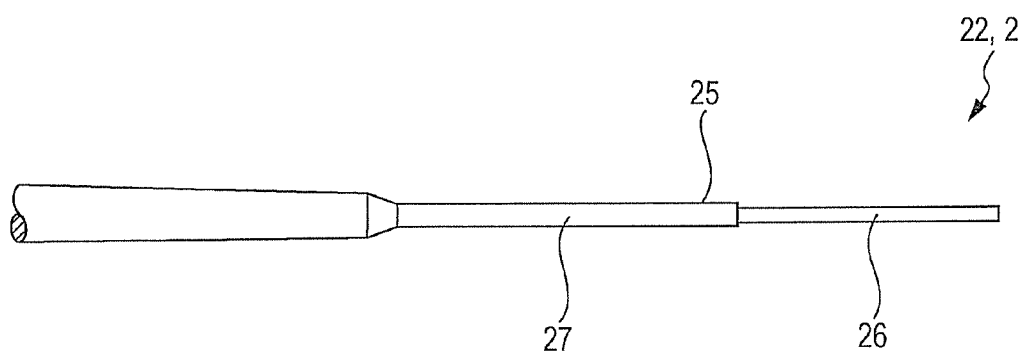
FIG. 3 is a partial side view of a core shaft of a guidewire according to a modification.
Figure 4:
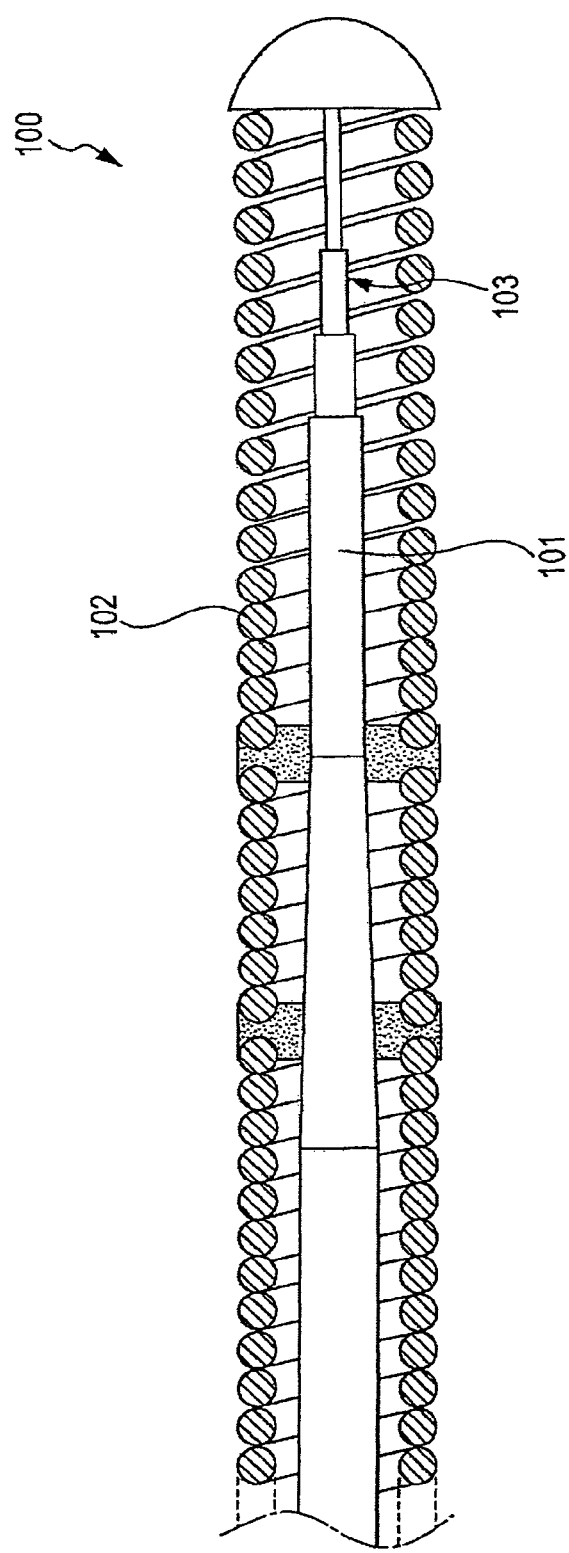
FIG. 4 is a sectional side view of a distal end portion of a guidewire of the related art.

As illustrated in FIG. 3, a part of the small-diameter portion 25 near to the distal end may be made of a stainless steel alloy (a first distal end portion 26), a part of the small-diameter portion 25 near to the proximal end may be made of a pseudoelastic alloy (a second distal end portion 27), and a part of the core shaft 2 between the small-diameter portion 25 and the proximal end the core shaft 2 may be made of a stainless steel alloy. With this structure, the pseudoelastic alloy improves the resilience of the distal end portion 22 of the core shaft 2. Moreover, because the portions made of a stainless steel alloy are provided to both sides of the part made of a pseudoelastic alloy (the second distal end portion 27), a torque applied to the proximal end portion of the guidewire 1 can be reliably transmitted to the distal end portion, so that the torque transmission and the operability of the guidewire 1 can be further improved.

In the first embodiment, the distal end portion 52 of the hollow stranded-wire coil 5 is tapered toward the distal end. Alternatively, the diameter of the distal end portion 52 may decrease stepwise toward the distal end.

In the first embodiment, the hollow stranded-wire coil 5 is made of only stainless steel strands. Alternatively, the hollow stranded-wire coil 5 may be made of only pseudoelastic alloy strands. With this structure, the resilience of the hollow stranded-wire coil 5 can be further increased. As a further alternative, the hollow stranded-wire coil 5 may be formed by combining stainless steel strands and pseudoelastic alloy strands (for example, three stainless steel strands and three pseudoelastic alloy strands). In this case, the stainless steel strands increase the rigidity of the hollow stranded-wire coil 5, while the pseudoelastic strands increase the resilience of the hollow stranded-wire coil 5. Therefore, the torque transmission, the operability, and the resilience of the guidewire 1 are improved.

In the first embodiment, the outer flexible tube 4 surrounds only the distal end portion of the core shaft 2. Alternatively, the outer flexible tube 4 may surround the entirety of the core shaft 2.

The present invention contains subject matter related to Japanese Patent Application No. 2009-143570 filed in the Japan Patent Office on Jun. 16, 2009, the entire contents of which are incorporated herein by reference.

What is claimed is:

1. A medical guidewire comprising:
   a core shaft including a distal end portion having a small diameter;
   an outer flexible tube that surrounds an outer periphery of the core shaft;
   an inner flexible tube disposed in the outer flexible tube surrounding the distal end portion of the core shaft, the guidewire being configured to have a first spacing of a gap between the inner flexible tube and the outer flexible tube, and to have a second spacing of a gap between the core shaft and the inner flexible tube, wherein the first and second spacings are varied along a length of the core shaft;
   a first joint that joins together: i) a distal end of the core shaft, ii) a distal end of the outer flexible tube, and iii) a distal end of the inner flexible tube; and
   at least one second joint that does not join the core shaft and joins the outer flexible tube to the inner flexible tube.

2. The medical guidewire according to claim 1, further comprising:
   a stranded wire disposed parallel to the distal end portion of the core shaft in the inner flexible tube between the at least one second joint and the distal end of the core shaft.

3. The medical guidewire according to claim 1, wherein the inner flexible tube has a tapered shape in which an outside diameter gradually decreases toward the distal end thereof, such that the first spacing of the gap between the inner flexible tube and the outer flexible tube expands toward a distal end of the medical guidewire.

4. The medical guidewire according to claim 3, wherein an inside diameter of the inner flexible tube is uniform from the distal end to a proximal end thereof.

5. The medical guidewire according to claim 1, wherein an outside diameter of the inner flexible tube decreases stepwise toward the distal end thereof, such that the first spacing of the gap between the inner flexible tube and the outer flexible tube expands toward a distal end of the medical guidewire.

6. The medical guidewire according to claim 5, wherein an inside diameter of the inner flexible tube is uniform from the distal end to a proximal end thereof.

7. The medical guidewire according to claim 1, wherein the inner flexible tube is a hollow stranded-wire coil in which a plurality of metal strands are stranded.

8. The medical guidewire according to claim 1, wherein
   the outer flexible tube is a single-wire coil including a large-pitch portion extending from the distal end of the outer flexible tube toward a proximal end of the outer flexible tube by a predetermined distance, the large-pitch portion having a pitch that is larger than a pitch of a proximal end portion of the outer flexible tube, and
   a proximal end of the large-pitch portion is positioned between the at least one second joint and the distal end of the outer flexible tube.

* * * * *